United States Patent

Di Battista et al.

Patent Number: 4,772,699
Date of Patent: Sep. 20, 1988

[54] DERIVATIVES OF MORPHOLINE CONTAINING SUBSTITUTED PIPERIDINE GROUPS

[75] Inventors: Piero Di Battista; Gilberto Nucida, both of Milan, Italy

[73] Assignee: Ausimont S.p.A., Milan, Italy

[21] Appl. No.: 2,940

[22] Filed: Jan. 13, 1987

[30] Foreign Application Priority Data

Jan. 13, 1986 [IT] Italy ................. 19070 A/86

[51] Int. Cl.$^4$ .......................... C07D 498/20
[52] U.S. Cl. .................. 544/71; 528/935
[58] Field of Search ......................... 544/71

[56] References Cited

U.S. PATENT DOCUMENTS 3,733,326  5/1973  Murayama et al. ............ 544/71 X

Primary Examiner—Richard L. Raymond
Attorney, Agent, or Firm—Stevens, Davis, Miller & Mosher

[57] ABSTRACT

Derivatives of morpholine containing substituted piperidine groups having the formula:

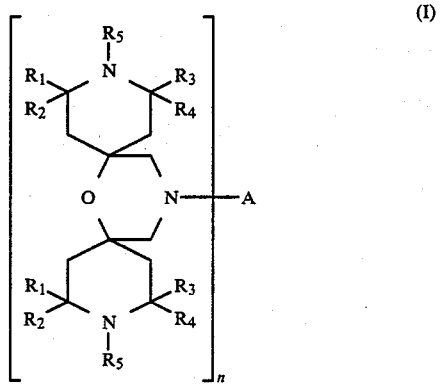

(I)

wherein
$R_1$, $R_2$, $R_3$ and $R_4$, the same or different, are each a lower alkyl group, or $R_1$ and $R_2$ and/or $R_3$ and $R_4$, together with a carbon atom to which they are bound, represent a cycloalkyl group or a group of the formula:

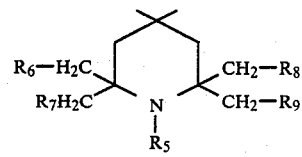

in which $R_6$, $R_7$, $R_8$ and $R_9$, the same or different, represent a hydrogen atom or a lower alkyl group, and $R_5$ represents a hydrogen atom, an alkyl group, an alkenyl group, an alkoxyalkyl group, an aralkyl group, a substituted aralkyl group carrying one or more substituents on the aryl radical, a 2,3-epoxypropyl group, a group of formula —CH$_2$—COOR$_{10}$ in which $R_{10}$ is an alkyl group, an alkenyl group, a phenyl group, an aralkyl group or a cyclohexyl group; a group of formula:

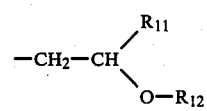

in which $R_{11}$ is a hydrogen atom, a methyl group, an ethyl group or a phenyl group, and $R_{12}$ is a hydrogen atom, an alkyl-substituted piperidyl group, a triazinyl group or an acyl group; an aliphatic acyl group or a group of formula —COOR$_{13}$ in which $R_{13}$ is an alkyl group, a benzyl group or a phenyl group;

A represents an organic group having n valence which does not adversely affect the polymer-stabilization activity; and n is an integer ranging from 1 to 3 depending on the valence of A.

The use of said derivatives as stabilizers for polymeric substances, and polymeric compositions stabilized with said piperidine-substituted morpholine derivatives.

8 Claims, No Drawings

DERIVATIVES OF MORPHOLINE CONTAINING SUBSTITUTED PIPERIDINE GROUPS

DESCRIPTION OF THE INVENTION

This invention relates to new derivatives of morpholine-containing substituted piperidine groups, to the use thereof as stabilizers for polymeric substances usually subject to worsening owing to thermal and/or photo-oxidation, and to the polymeric compositions stabilized with said derivatives.

As is well known, heat, oxygen and light, especially the actinic radiations existing in the low wave-length ultraviolet band, badly affect the appearance and the properties of organic polymers. For example polyesters which are usually colorless yellow when exposed to sunlight. Analogously, the oxidation rate of polyolefins when exposed to air is highly increased due to ultraviolet light; polystyrene becomes yellow and brittle, with corresponding loss of its desirable properties, when exposed to actinic light, etc. The same degradation and alteration effects of the mechanical properties occur also when the polymeric materials are subjected to heat treatments, as happens for example during their transformation into formed or shaped articles such as films, fibers and the like.

With a view to stabilizing polymeric materials and to retianing unaltered the desirable properties thereof, it is a usual practice to add to them one or more stabilizers, the function of which is that of opposing the susceptibility of such polymeric materials of undergoing an oxidative and thermal degradation.

One particular type of stabilizers which have been very successful are the sterically hindered amines (HALS) and, in particular, derivatives of alkyl-substituted piperidine. The hindered amines based on alkyl-substituted piperidine, though excellent stabilizers for polymeric substances generally subject to worsening, are not suited to be utilized with the same good results in all polymeric substances and for all technological uses. In fact, these known stabilizers have the drawback of not possessing all those parameters and technical characteristics necessary for all the technological applications such as low volatility, resistance to migration, thermal stability, insolubility in water, etc., etc.

Thus, it is an object of the present invention to improve the properties of the known stabilizers containing alkylsubstituted piperidine radicals.

It has now been found that this and still further objects are achieved from derivatives of morpholine-containing substituted piperidine groups having the formula:

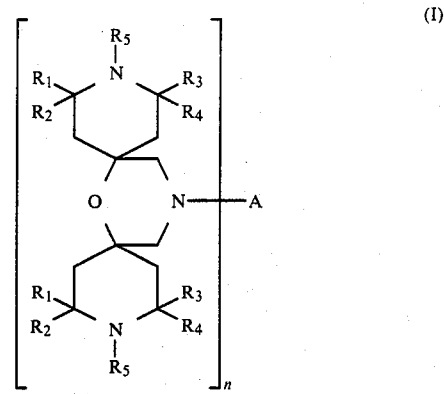
(I)

in which:

$R_1$, $R_2$, $R_3$, and $R_4$, which may be like or unlike one another, are each a lower alkyl group, or $R_1$ and $R_2$ and/or $R_3$ and $R_4$, along with a carbon atom to which they are bound, represent a cycloalkyl group or a group of the formula:

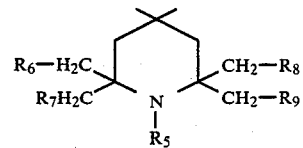

in which $R_6$, $R_7$, $R_8$ and $R_9$, which may be like or unlike one another, are a hydrogen atom or a lower alkyl group, and $R_5$ is a hydrogen atom; an alkyl group; an alkenyl group; an alkoxyalkyl group; either nonsubstituted or carrying one or more substituents on the aryl radical; a 2,3-epoxypropyl group, a group of formula $-CH_2-COOR_{10}$ in which $R_{10}$ is an alkyl group; an alkenyl group, a phenyl group; an aralkyl group or a cyclohexyl group; a group of the formula:

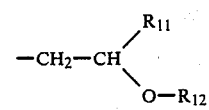

in which $R_{11}$ is a hydrogen atom, a methyl group, an ethyl group or a phenyl group, and $R_{12}$ is a hydrogen atom, an alkyl-substituted piperidyl group, a triazinyl group or an acyl group; an aliphatic acyl group, or a group of formula $-COOR_{13}$ in which $R_{13}$ is an alkyl group, a benzyl group or a phenyl group;

A represents an organic radical having n valence which does not adversely affect the stabilizing activity of the polymer; and n is an integer from 1 to 3, depending on the valence of A.

According to the present invention, it has also been found that the derivative of morpholine containing substituted piperidine groups having the formula (I), either alone or in admixture with other known stabilizers, efficaciously stabilize a wide range of polymers against photo and thermal degradation and, furthermore, that they are highly compatible with polymers and in particular with polyolefins.

The term "lower alkyl", whenever used herein and in the annexed claims, means an alkyl containing up to 6 carbon atoms.

In the above-reported formula (I), when $R_1$, $R_2$, $R_3$ or $R_4$ represents an alkyl group, this is preferably an alkyl group containing from 1 to 4 carbon atoms, such as, e.g., methyl, ethyl, propyl, isopropyl, butyl or isobutyl; and of these the methyl group is preferred.

$R_1$ and $R_2$ and/or $R_3$ and $R_4$, along with the carbon atom to which they are bound, may represent a cycloalkyl group containing from 5 to 7 carbon atoms, such as, e.g., cyclopentyl, cyclohexyl, cycloheptyl, etc., or an alkyl-substituted piperidyl group, such as for example:

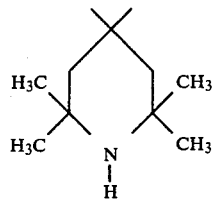

When $R_5$ is an alkyl group, it may contain from 1 to 8 carbon atoms. In practice, it is preferable that the alkyl group $R_5$ shall contain from 1 to 4 carbon atoms; and of these, the methyl group is particularly preferred.

When $R_5$ is an alkenyl group, it may contain from 3 to 6 carbon atoms, such as e.g., the allyl group, the 2-butenyl group, or the 2-hexenyl group. The alkenyl group containing 3 or 4 carbon atoms is the preferred one, and among said groups the allyl group is particularly preferred.

When $R_5$ is an alkoxyalkyl group, it may be an alkoxyalkyl group containing from 1 to 3 carbon atoms in the alkyl chain and from 1 to 18 carbon atoms in the alkoxy chain. Examples of alkoxyalkyl groups are: methoxymethyl, ethoxymethyl, 2-butoxyethyl, 3-butoxypropyl, 2-octoxyethyl, 2-octadecyloxyethyl. The alkoxyalkyl groups containing on the whole 2 to 6 carbon atoms are preferred.

When $R_5$ is an aralkyl group, it may preferably contain from 7 to 15 carbon atoms and it may be unsubstituted or substituted with up to 3 substituents on the aryl radical. Chlorine atoms, alkyl groups with 1 to 4 carbon atoms, alkoxy groups with 1 to 8 carbon atoms, or hydroxy groups may be used as substituents. Typical examples of aralkyl groups are: benzyl, p-chlorobenzyl, o-chlorobenzyl, m-chlorobenzyl, o-methylbenzyl, m-methylbenzyl, p-methylbenzyl, p-isopropylbenzyl, p-ter-butylbenzyl, p-methoxybenzyl, p-butoxybenzyl, p-octoxybenzyl, 4-hydroxy-3,5-di-ter-butylbenzyl, etc.

When $R_5$ represents a group of formula —$CH_2$—$COOR_{10}$, $R_{10}$ may represent:

an alkyl group containing preferably from 1 to 18 carbon atoms, such as methyl, ethyl, isopropyl, butyl, isobutyl, t-butyl, isopentyl, octyl, dodecyl, octadecyl, etc.;

an alkenyl group preferably containing from 3 to 6 carbon atoms, such as allyl, 2-butenyl, 2-hexenyl, etc.;

a phenyl group; or an aralkyl group, preferably containing 7 or 8 carbon atoms, or a cyclohexyl group.

Of these, the alkyl group containing from 1 to 4 carbon atoms is the preferred one.

When $R_5$ represents the group

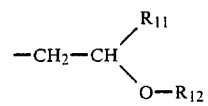

$R_{11}$ represents a hydrogen atom, a methyl group or a phenyl group and $R_{12}$ represents a hydrogen atom, an alkyl group containing from 1 to 4 carbon atoms, an acyl group, for example an aliphatic, araliphatic, aromatic or alicyclic acyl group.

Particularly preferred are the groups of formula —$CH_2$—$CH_2$—O—$R_{12'}$ in which $R_{12}$ has one of the values cited hereinbefore.

When $R_5$ is an aliphatic acyl group, it may preferably contain up to 4 carbon atoms and it is preferably a saturated or unsaturated acyl group, such as e.g., formyl, acetyl, acrylyl or crotonyl.

When $R_5$ is a group of formula —$COOR_{13}$, $R_{13}$ is an alkyl group, preferably with 1 to 8 carbon atoms, such as methyl, ethyl, isobutyl, heptyl; a benzyl group or a phenyl group.

Generally speaking, group A represents a hydrogen atom, an alkyl or alkenyl residue containing up to 18 carbon atoms, which may be either substituted or unsubstituted; an aliphatic arylaliphatic, aromatic or alicyclic acyl or diacyl residue containing up to 20 carbon atoms; or an heterocyclic group. In particular, the following groups are the preferred ones:

When n=1

A preferably represents:

a hydrogen atom;

an aliphatic, aryl-aliphatic, alicyclic, aromatic or heterocyclic acyl group, preferably an acyl group containing up to 18 carbon atoms and, even better, a group of formula —$COR_{19}$ in which $R_{19}$ represents a hydrogen atom; an alkyl group with 1 to 17 carbon atoms such as methyl, ethyl, propyl, isopropyl, butyl, ter-butyl, pentyl, isopentyl, 1-ethylpentyl, nonyl, undecyl, pentadecyl, etc.; an alkenyl group with 2 to 5 carbon atoms, such as vinyl, 1-propenyl, 2-methyl-1-propenyl, isopropenyl, or 1,3-pentadienyl; an alkynyl group with 2 or 3 carbon atoms, such as ethynyl or propynyl; a phenyl group either non-substituted or substituted with up to 3 substituents either like or unlike, such as chlorine, alkyl with 1 to 4 carbon atoms, alkoxy with 1 to 8 carbon atoms, hydroxy or nitro (such as for example phenyl, o-chlorophenyl, m-chlorophenyl, p-chlorophenyl, o-methylphenyl, m-methylphenyl, p-methylphenyl, p-isopropylphenyl, p-ter-butylphenyl, m-methoxyphenyl, p-methoxyphenyl, p-octoxyphenyl, o-hydroxyphenyl, 2-hydroxy-3-methylphenyl, 4-hydroxy-3,5-di-ter-butylphenyl, m-nitrophenyl, etc.); a naphthyl group; a styryl group; an aralkyl group with 7 to 15 carbon atoms, which may be either non-substituted or substituted with up to 3 like or unlike substituents such as chlorine, alkyl with 1 to 4 carbon atoms, alkoxy with 1 to 8 carbon atoms or hydroxy (such as benzyl, phenethyl, 4-hydroxy-3,5-di-ter-butylbenzyl or 4-hydroxy-3,5-diterbutylphenethyl); a phenoxymethyl group; a cyclohexyl group; a 2-pyridyl group; a 3-pyridyl group; a 4-pyridyl group; a 2-furyl group;

a group of formula —CO—$R_{20}$—COOH, in which $R_{20}$ is an alkylene group preferably containing from 1 to 10 carbon atoms, the chain of which may be interrupted by an atom of oxygen or of sulphur; or a metal salt thereof in which the metal may be, for example, barium, nickel, manganese, calcium, zinc, iron, sodium, cobalt or tin; or a lower alkyl ester thereof in which the alkyl chain contains from 1 to 4 carbon atoms, such as methyl, ethyl, propyl, butyl esters, etc.;

a group of the formula:

$$-CO-N\begin{matrix}R_{21}\\ R_{22}\end{matrix}$$

in which $R_{21}$ is hydrogen; an alkyl group containing 1 to 4 carbon atoms; an aralkyl group preferably containing 7 or 8 carbon atoms; a phenyl group; and $R_{22}$ is an alkyl group containing from 1 to 18 carbon atoms, an aryl group preferably containing from 6 to 10 carbon atoms, optionally substituted by one or more chlorine atoms and/or alkyl groups with from 1 to 4 carbon atoms, such as for example phenyl, o-chlorophenyl, p-chlorophenyl, o-, m-, or p-toluyl, alpha-naphthyl or beta-naphthyl, an aralkyl group containing 7 or 8 carbon atoms, or a cyclohexyl group. As an alternative, $R_{21}$ and $R_{22}$, together and with the nitrogen atom to which they are bound may represent a piperidine group, a 1-pyrrolidinyl group or a morpholine group. Among these groups, those having the formula $-CO-N-H-R_{22}$, in which $R_{22}$ is the same as specified hereinbefore, are particularly preferred;

an alkyl group preferably containing from 1 to 18 carbon atoms, such as methyl, ethyl, butyl, octyl, dodecyl or octadecyl;

an alkenyl group preferably containing from 3 to 6 carbon atoms, such as allyl, 2-butenyl, methallyl or 2-hexenyl;

an aralkyl group with from 7 to 9 carbon atoms and optionally carrying up to 3 substituents in the aryl chain, such as an alkyl with from 1 to 4 carbon atoms and/or a hydroxy, such as for example benzyl, p-methylbenzyl, p-isopropylbenzyl; 4-hydroxy-3,5-di-ter-butylbenzyl or 3-(4-hydroxy-3,5-di-ter-butylphenyl)-propyl;

a cyclohexyl group;

a group of the formula:

$$-\underset{\underset{R_{23}}{|}}{C}=CH-COOR_{24}$$

in which $R_{23}$ is a hydrogen atom, a methyl or lower alkyl group or a phenyl group, and $R_{24}$ an alkyl group containing preferably from 1 to 8 carbon atoms;

an alkylene alkyl-substituted piperidinyl group of the formula in which m is an integer between 1 and 6 and $R_1$, $R_2$, $R_3$, $R_4$, $R_5$ have the above-reported meanings.

When n=2

A represents:

an aliphatic, araliphatic, aromatic, alicyclic or heterocyclic diacyl, preferably containing up to 12 carbon atoms and, preferably, a group of formula $-CO-(R_{25})_p-CO-$ in which p may be 0 or 1 and $R_{25}$ an alkylene group with 1 to 20 carbon atoms either linear or branched, optionally containing an alkylbenzyl or hydroxy-alkylbenzyl group, and the chain of which may be interrupted by an atom of sulphur or of oxygen; an alkylene group with from 2 to 4 carbon atoms; a phenylene group; a cyclohexylene group; a 2-4-pyridindiyl group; a 2,5 pyridindiyl group or a thiophendiyl group; a carbonyl group;

a group of the formula $$-CO-\underset{\underset{R_{21}}{|}}{N}-R_{26}-\underset{\underset{R_{21}}{|}}{N}-CO$$

in which $R_{21}$ is the same as indicated hereinabove, and $R_{26}$ represents an alkylene group preferably containing from 2 to 10 carbon atoms; an arylene group having preferably from 6 to 10 carbon atoms and optionally substituted such as o-phenylene, m-phenylene, p-phenylene, 2,4-toluidine, 1,5-naphthylene, etc., a xylylene group, a cyclohexylene group such as 1,4-cyclohexylene;

a group of the formula in which $R_{27}$ may be an oxygen atom or an alkylene group containing from 1 to 4 carbon atoms;

a group of the formula:

in which $R_{28}$ may be a hydrogen atom or a methyl group;

a group of the formula:

such as 4,4-methylene-bis(dicyclohexyl);

or a group of the formula such as for example 1,3-cyclohexylene-dimethylene, etc.; among the groups comprised in this formula, those of formula —CO—NH—$R_{27}$—NH—CO—, in which $R_{27}$ has the values defined hereinbefore, are the preferred ones;

an alkylene group containing up to 10 carbon atoms and preferably from 2 to 6 carbon atoms, such as ethylene, tetramethylene, hexamethylene, etc.;

an alkenylene group containing from 4 to 10 carbon atoms;

a xylylene group, such as o-xylylene, m-xylylene, p-xylylene, etc.;

a group of the formula:

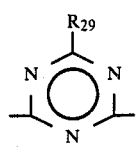

in which $R_{29}$ may be a hydrogen atom, an alkyl radical having from 1 to 18 carbon atoms, the

or —O—$R_{32}$ radical, wherein $R_{30}$, $R_{31}$ and $R_{32}$, the same or different, may be an alkyl radical having from 1 to 18 carbon atoms, the group

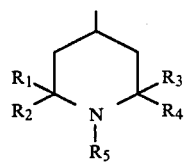

or $R_{30}$ and $R_{31}$ together with the N atom to which they are bound form a cyclic group which may contain or does not contain other hetero-atoms, as, e.g., an N or an O atom, such as piperidine, pyrrolidino, morpholino or piperazino.

When n=3

A preferably may be:

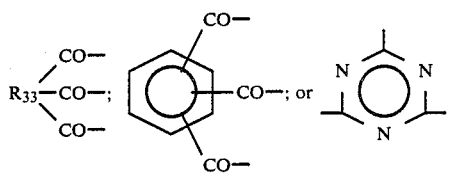

in which $R_{33}$ may be a linear or cyclic alkyl group having from 1 to 18 carbon atoms.

The derivatives of the morpholine containing substituted piperidine groups which are particularly preferred are those of the formula:

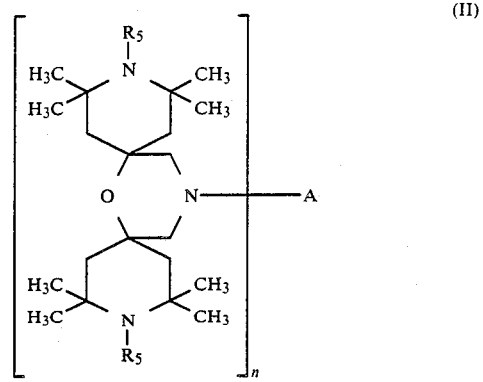
(II)

in which $R_5$ is a hydrogen atom, a methyl group, a benzyl group, a 2,3-epoxypropyl group, or a group of the formula —$CH_2$—$CH_2$—O—$R_{12}$ in which $R_{12}$ is hydrogen or an alkyl group with from 2 to 18 carbon atoms or a benzoyl group; n=1, 2 or 3; and

When n=1

A represents a hydrogen atom, an alkyl radical containing up to 6 carbon atoms, a group of the formula —CO—$R_{19}$ in which $R_{19}$ represents an alkyl group with from 1 to 17 carbon atoms, a phenyl group optionally substituted by up to 3 alkyl radicals with from 1 to 4 carbon atoms and/or with a hydroxy radical, or 4-hydroxy-3,5-di-tert-butylphenethyl; or a group of the formula —CO—NH—$R_{22}$ in which $R_{22}$ represents an alkyl group with from 1 to 18 carbon atoms, a phenyl group, or a cyclohexyl group;

When n=2

A represents an alkylene radical containing up to 6 carbon atoms —CO—; a group of the formula —CO—$(R_{25})_p$—CO— in which p is 0 or 1 and $R_{25}$ represents an alkenyl group with 1 to 10 carbon atoms; the group —$CH_2$—$CH_2$—S—$CH_2$—$CH_2$; a phenylene group; a group of the formula:

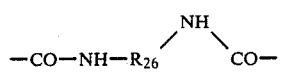

in which $R_{26}$ represents the hexamethylene radical, the 2,4 toluylene radical; the methylene-di-p-phenylene radical; or a triazine radical:

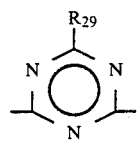

in which $R_{29}$ represents

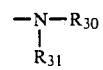

or —O—$R_{32}$ in which $R_{30}$, $R_{31}$ and $R_{32}$ represent an alkyl radical having from 1 to 8 carbon atoms or the group When $n=3$ A preferably is:

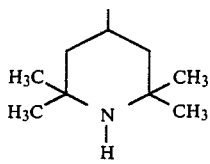

or $R_{30}$ and $R_{31}$ together with the N atom form the morpholino group.

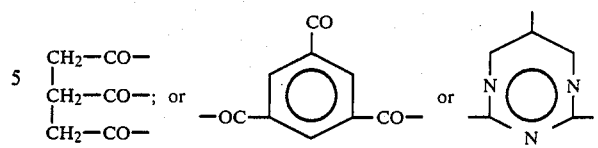

The particularly preferred compounds are those of formula (II) in which $n=1$ and A represents a group of the formula $-CO-R_{19}$; or $n=2$ and A represents a group of the formula $-CO-R_{25}-CO-$ with $R_{19}$ and $R_{25}$ having the values defined hereinbefore.

A non-limiting list of derivatives of the morpholine containing substituted piperidine groups is given hereinbelow, and the numbers which refer to the products will be utilized to identify them also in the examples:

| COMPOUND | $R_5$ | n | A |
|---|---|---|---|
| 1 | —H | 1 | —H |
| 2 | —H | 1 | —CH$_3$ |
| 3 | —H | 1 | —nC$_4$H$_9$ |
| 4 | —H | 1 | —CH$_2$—C$_6$H$_5$ |
| 5 | —H | 1 | —CH$_2$—(3,5-di-tBu-4-OH-C$_6$H$_2$) |
| 6 | —H | 1 | —CO—CH$_3$ |
| 7 | —H | 1 | —CO—C$_{11}$H$_{23}$ |
| 8 | —H | 1 | —CO—C$_{17}$H$_{35}$ |
| 9 | —H | 1 | —CO—C$_6$H$_5$ |
| 10 | —H | 1 | —CO—(3,5-di-tBu-4-OH-C$_6$H$_2$) |
| 11 | —CH$_3$ | 1 | —H |
| 12 | —CH$_3$ | 1 | —CH$_3$ |
| 13 | —CH$_3$ | 1 | —CH$_2$—CH=CH$_2$ |
| 14 | —CH$_3$ | 1 | —CO—CH$_2$—CH$_2$—(3,5-di-tBu-4-OH-C$_6$H$_2$) |
| 15 | —CH$_3$ | 1 | —CO—CH=CH—CH$_3$ |

-continued

| COMPOUND | $R_5$ | n | A |
|---|---|---|---|
| 16 | $-CH_3$ | 1 | 4,6-bis(diethylamino)-5-methyl-1,3,5-triazin-2-yl group (triazine with two $-N(C_2H_5)_2$ substituents and a methyl) |
| 17 | $-CH_3$ | 1 | 4,6-bis[N-n-butyl-N-(2,2,6,6-tetramethylpiperidin-4-yl)amino]-1,3,5-triazin-2-yl (methyltriazine with two $-N(nC_4H_9)-$(2,2,6,6-tetramethylpiperidin-4-yl) groups) |
| 18 | $-CH_2-CH=CH_2$ | 1 | $-CH_2-CH=CH_2$ |
| 19 | $-CH_2-C_6H_5$ | 1 | $-CH_2-C_6H_5$ |
| 20 | $-CH_2-C_6H_5$ | 1 | $-CO-NH-C_6H_5$ |
| 21 | $-CH_2-CH_2OH$ | 1 | $-CH_2CH_2OH$ |
| 22 | $-CH_2-CH_2-CO_2-CH_3$ | 1 | $-CH_2-CH_2-CO_2-CH_3$ |
| 23 | H | 2 | $-CO-$ |
| 24 | H | 2 | $-CO-CO-$ |
| 25 | H | 2 | $-CO-CH_2-CO-$ |
| 26 | H | 2 | $-CO-(CH_2)_4-CO-$ |
| 27 | H | 2 | $-CO-C(nC_4H_9)(CH_2-[3,5-di-tBu-4-hydroxyphenyl])-CO-$ |
| 28 | H | 2 | phthaloyl (benzene-1,2-di(CO−)) |
| 29 | H | 2 | cyclohexane-1,4-dicarbonyl ($-CO-C_6H_{10}-CO-$) |
| 30 | $-CH_3$ | 2 | $-CO-CH_2-CO-$ |
| 31 | $-CH_3$ | 2 | $-CO-NH-(CH_2)_6-NH-CO-$ |
| 32 | $-CH_3$ | 2 | $-CO-NH-$(2-methyl-1,4-phenylene)$-NH-CO-$ |
| 33 | $-CH_3$ | 2 | $-CH_2-CH_2-$ |
| 34 | $-CH_3$ | 2 | $-CH_2CH=CH-CH_2-$ |

-continued

| COMPOUND | R5 | n | A |
|---|---|---|---|
| 35 | —CH3 | 2 | —CH2—⟨C6H4⟩—CH2— (para) |
| 36 | —CH3 | 2 | 2,6-dimethyl-1,3,5-triazin-4-yl-N(n-C4H9)2 |
| 37 | —CH3 | 2 | triazinyl with N(n-C4H9) linked to 2,2,6,6-tetramethylpiperidin-4-yl |
| 38 | H | 3 | CH2—CO— / CH—CO— / CH2—CO— |
| 39 | —CH3 | 3 | 1,3,5-benzenetricarbonyl (三 C=O) |
| 40 | —CH3 | 3 | 2,4,6-trimethyl-1,3,5-triazinyl |

The derivatives of the morpholine containing substituted piperidine groups of the formula (I) are synthesized according to conventional methods by means of the processes indicated hereinbelow.

Method A

The compounds of the formula (I), where A is hydrogen, are synthesized by reaction of a compound of the formula (III) with ammonia, according to the reaction:

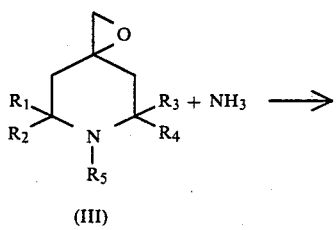

(III)

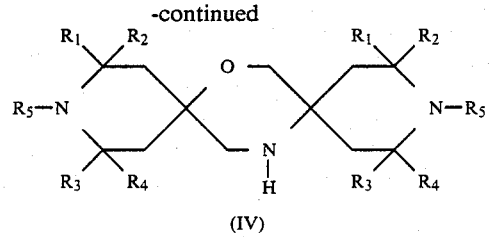

(IV)

wherein $R_1$, $R_2$, $R_3$, $R_4$ and $R_5$ are defined as hereinbefore.

Method B

The compounds of the formula (I), wherein A is the acyl group, a diacyl group, a carbonyl group, the group:

$$\underset{\text{benzene ring}}{\bigcirc}\begin{matrix}-CO-\\-CO-\\-CO-\end{matrix}$$

or the group:

$$\begin{matrix} CH_2CO- \\ | \\ CH-CO \\ | \\ CH_2-CO- \end{matrix}$$

are obtainable by reacting a compound of the formula (IV) with a reactive derivative of the acid corresponding to group A, for example with a halide or a lower alcohol ester.

Method C

The compounds of the formula (I) in which A represents an alkyl, alkenyl, aralkyl group, a cyclohexyl group, an alkylene group, an alkenylene group, or a xylylene group, are synthesized by reacting a compound of the formula (IV), as already defined, with a halide of group A.

Method D

The compounds of the formula (I), wherein A represents one of the groups —CONHR$_{22}$ or —CONHR$_{26}$—NH—CO—, may be prepared by reacting a compound of the formula (IV), as already defined, with an isocyanate of the formula R$_{22}$NCO or OCN—R$_{26}$—N—CO.

Method E

The compounds of the formula (I), wherein A represents one of the groups $$-CON\begin{matrix}R_{21}\\ \\R_{22}\end{matrix} \quad \text{or} \quad -CON-R_{26}-N-CO-,\begin{matrix}|\\R_{21}\end{matrix}\begin{matrix}|\\R_{21}\end{matrix}$$

are synthesized by reacting a compound of the formula (IV), as already defined, with the carbamoyl chloride obtained by reacting phosgene with an amine of the type $$H-N\begin{matrix}R_{21}\\ \\R_{22}\end{matrix} \quad \text{or} \quad HN-R_{26}-NH\begin{matrix}|\\R_{21}\end{matrix}\begin{matrix}|\\R_{21}\end{matrix}$$

Method F

The compounds of the formula (I), in which A represents the group —CO—R$_{20}$—COOH, are synthesized by reacting a compound of the formula (IV), as already defined, with an anhydride of the formula:

$$R_{20}\begin{matrix}CO\\ \\CO\end{matrix}O$$

The esters and the salts of this group may be easily prepared according to conventional methods.

Method G

The compounds of the formula (I), wherein A represents a group $$-C=CH-COOR_{24},\\ |\\R_{23}$$

may be prepared by reacting a compound of the formula (IV), as already defined, with a compound of the formula R$_{23}$—C≡C—COOR$_2$.

Method H

The compounds of formula (I), where A represents a group $$\begin{matrix}|\\(CH_2)\\ \\ R_1\diagup\overset{OH}{\underset{\underset{R_5}{|}}{\bigcirc}}\diagdown R_3\\R_2\quad N\quad R_4\end{matrix}$$

are synthesized by reacting a compound of formula (IV), as already defined, with a compound of the formula:

$$\begin{matrix}\overset{O}{\triangle}\\R_1\diagup\underset{\underset{R_5}{|}}{\bigcirc}\diagdown R_3\\R_2\quad N\quad R_4\end{matrix}$$

When R$_5$ is a group other than hydrogen, this may be introduced into the compound, prior to or after the introduction of A, by one of the following methods.

Method J

The compounds in which R$_5$ represents an alkyl group, an alkoxyalkyl group, an aralkyl group, a 2-3 epoxypropyl group, the group —CH$_2$—COO—R$_{10}$, the group $$-CH_2-CH\begin{matrix}\diagup R_{11}\\ \\\diagdown O-R_{12}\end{matrix},$$

an aliphatic acyl group, or the group —COOR$_{13}$ (R$_{10}$, R$_{11}$, R$_{12}$, R$_{13}$ are the same as defined hereinbefore), may be easily prepared by reacting the corresponding compounds in which R$_5$ is a hydrogen atom with a halide of the group R$_5$.

Method K

The compounds in which R$_5$ represents the group

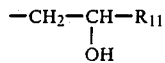

($R_{11}$ being defined as hereinbefore) may be prepared by reacting the corresponding compounds, in which $R_5$ is the hydrogen atom, with an epoxide, such as ethylene oxide, propylene oxide, styrene oxide. The resulting compounds may be acylated to obtain the corresponding acylated compounds.

Method L

The compounds in which $R_5$ represents a methyl group are synthesized according to the Leuckart-Wallach reaction, i.e., by reacting the corresponding compound in which $R_5$ represents the hydrogen atom, with formic acid or formaldehyde.

Method M

The compounds in whcih $R_5$ represents a formyl group, may be prepared by reacting a corresponding compound, in which $R_5$ is a hydrogen atom, with ethyl orthoformate, in the presence of an acid catalyst.

The compounds of formula (III), which represent the starting substances for preparing the derivatives of morpholine having the formula (I), utilized in the polymeric compositions according to the present invention, may be prepared according to the teachings of U.S. Pat. No. 4,400,513.

The derivatives of the morpholine containing substituted piperidine groups of the formula (I) are useful to stabilize polymers, in particular synthetic polymers, against photo- and thermal-degradation.

Examples of polymers which may be stabilized according to the present invention are:

polymers of olefins and of dienes, such as: homopolymers of olefins and of dienes (e.g., low density polyethylene, high density polyethylene, cross-linked polyethylene, polypropylene, polyisobutene, polymethylbutene-1, polymethyl-pentene-1, polyisoprene, polybutadiene, mixtures of such homopolymers or copolymers (for example, ethylene-propylene copolymers, propylene-butene-1 copolymers), or ethylene-propylene terpolymers with dienes such as hexadiene, dicyclopentadiene, etc.

styrene polymers, such as: polystyrene, copolymers of styrene and alpha-methylstyrene with acrylonitrile, methyl methacrylate, acrylic esters, styrene polymers modified with elastomers, grafted styrene polymers, etc.;

halogenated vinyl and vinylidene polymers, such as: poly-vinyl-chloride, poly-vinylidene-chloride, poly-vinyl-fluoride, polychloroprene, vinyl chloride/vinylidene chloride copolymers, vinyl chloride/vinyl acetate copolymers, vinylidene chloride/vinyl acetate copolymers, etc.;

polymers deriving from $\alpha$-$\beta$ unsaturated acids, such as: polyacrylates, polymethacrylates, polyacrylonitrile, polyacrylic amides;

polymers derived from alcohols and from unsaturated amines and acylated or acetal derivatives thereof, such as polyvinyl alcohol, polyvinyl acetate, polyallyl-melamine and copolymers thereof with other ethylenically unsaturated monomers;

epoxide polymers;
polyacetals;
polyurethanes and polyureas;
polycarbamates;
polysulphones;
polyamides and copolyamides;
polyesters;
cross-linked polymers derived from aldehydes, from phenols, from ureas, or from melamines;
alkyd resins;
unsaturated polyester resins;
natural polymers, such as cellulose, rubber, proteins or chemically modified analogues thereof (e.g., cellulose acetate), etc.

The proportion of the morpholine derivatives of the formula (I) necessary to efficaciously stabilize the polymers depends on various factors, such as the type and properties of the polymer, the use for which it is intended, and the simultaneous presence of other stabilizers.

Generally, such amounts range from 0.01 to 5% by weight of stabilizer based on the polymer. In particular, the preferred amount ranges from 0.02 to 1% for the polymers of olefins, dienes and styrene; from 0.02 to 0.5% for the polymers of vinyl and vinylidene; from 0.02 to 2% for polyurethanes and polyamides.

Optionally, two or more stabilizers having the formula (I) may be utilized.

The morpholine derivatives of formula (I) utilized as stabilizers in the polymeric compositions according to this invention may be easily incorporated into the polymers to be stabilized according to conventional operating methods, e.g., the stabilizers may be mixed with the polymer in the form of a dry powder, or a stabilizer solution or suspension or emulsion may be admixed with a polymer solution or suspension or emulsion.

The morpholine derivatives containing substituted piperidine groups of the formula (I) may be employed either alone or in admixture with other known additives such as antioxidants, UV-ray absorbers, pigments, fillers, basic nitrogenous polycondensates, stabilizers, and the like.

Examples of such additives are oxybenzotriazoles, oxybenzophenones, Ni stabilizers, metal soaps, phenolic antioxidants, phosphites, phosphinites, thioesters, hydroquinone derivatives, triazinic compounds, acylamino-phenols, benzyl-phosphates, sterically hindered phenols such as 4,4'-bis-butylidene-bis-(2,6-di-tert-butyl-phenol); triazino-phenol compounds, etc.

Such additives may be utilized along with the compounds having formula (I), according to the present invention, in a weight ratio ranging from 0.5:1 to 3:1.

For a still better understanding of the present invention and as an aid to practicing the same, there are reported hereinbelow a few illustrative preferred examples which however are not to be considered a limitation of the invention.

In the examples, all parts are by weight, unless otherwise specified.

EXAMPLE 1

Preparation of Compound No. 1

3,11,15-triaza-7-oxa-2,2,4,4,10,10,12,12,-octamethyl-di-spiro(5,1,5,3)hexadecane, 33.8 g of 2,2,6,6-tetramethyl-piperidyl-4-spirooxirane (0.2 m) in 100 cc of methanol and 6.5 g (0.1 m) of $NH_4OH$ containing 30% by weight of water, were charged into a steel autoclave (0.5 l) equipped with a magnetic stirrer. The reaction mixture was maintained under stirring at the temperature of 150° C. for 5 hours.

The solvent was evaporated and the residue was dissolved in CH₃CN. By cooling, a product crystallizes having a melting point of 109°–111° C., which at the percentage analyses gave the following results:

C=71%
H=11.8%
N=12.6%

The product was recognized by N.M.R., I.R. and mass analyses as corresponding to the formula:

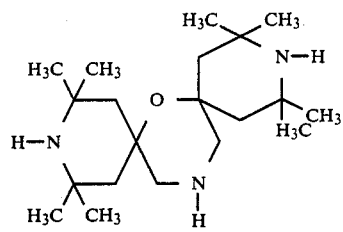

having the following theoretical percentages:
C=71.2%
H=11.6%
M=12.46%

EXAMPLE 2

Preparation of Compound No. 11

By operating according to the same procedures as in Example 1, from 1,2,2,6,6-pentamethyl-4-spiro-oxirane there was obtained 3,11,15-triaza-7-oxa-2,2,3,4,4,10,10,11,12,12-decamethyl-di-spiro-(5,1,5,3)-hexadecane having a melting point of 82°–85° C. (compound No. 11).

EXAMPLE 3

Preparation of Compound No. 25

19 g (0.056 m) of the 3,11,15-triaza-7-oxa-2,2,4,4,10,10,12,12-octamethyl-di-spiro-(5,1,5,3)-hexadecane of Example 1 were mixed with 4.5 g of di-ethyl malonate.

The reaction mixture was heated at 160° C., under stirring.

Ethyl alcohol coming from the reaction mixture was collected into a dry ice-ethyl alcohol trap.

After about 3 hours of heating, vacuum was applied and ethyl alcohol was continuously distilled.

The vacuum was increased up to 15 mm of Hg and contemporaneously the temperature was increased up to 180° C.

The reaction mixture was maintained under these conditions until complete evolution of the reaction ethyl alcohol (about 6 hours), after which it was cooled down under a nitrogen atmosphere and the residue thus obtained was crystallized from hexane.

12 g of product were obtained, having a melting point of 167°–170° C., which, on the basis of IR, N.M.R. and mass spectrophotometric analyses, was recognized as:

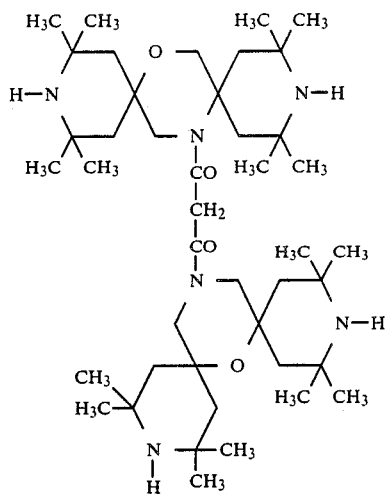

EXAMPLE 4

Preparation of Compound No. 30

By operating according to the same procedures as in Example 1, the N-methyl derivative of the product obtained in Example 3 was prepared by using 0.056 moles of 3,11,15-triaza-7-oxa-2,2,3,4,4,10,10,11,12,12-decamethyl-di-spiro-(5,1,5,3)-hexadecane.

A product having a melting point of 139°–142° C. was obtained, which by I.R., N.M.R. and mass spectrophotometric analyses was recognized as:

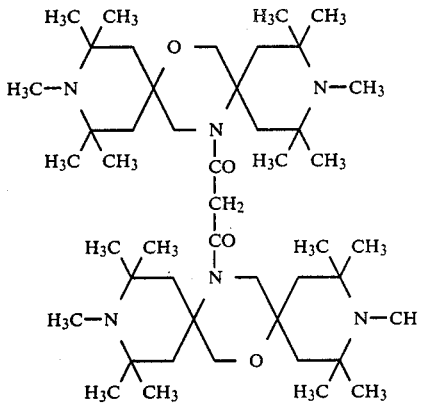

STABILIZATION TEST

To 300 g of non-stabilized polypropylene having an intrinsic viscosity, measured at 130° C. in tetralin, of 162 cc/g, a residue of 96.5% upon extraction with heptane, and an ash content of 80 ppm, there were added 200 cc of chloroform containing, dissolved therein, one of the compounds reported in the table. The amount of added compound was 0.25% by weight based on the polypropylene.

The mixture was stirred during about 6 hours, at room temperature, in a rotary evaporator, then it was dried at 0.01 mm of Hg and at 50° C. for 1 hour. The resulting powder was extruded in a Brabender exruder at 220° C. and granulated. The granules were converted to films having a uniform thickness of 50–60 microns.

On the films so obtained there was determined the photo-oxidative stability, considered as the time required to obtain the rupture of the film by one bending by 180°, after exposure to Xenotest 1200 under the following conditions:

Black panel temperature: 43+/−2 WC
Relative humidity:
Alternate exposure - the obtained results were:

| Compound No. | Embrittlement Time In Hours |
|---|---|
| (Control) | 100 |
| 1 | 1200 |
| 11 | 1000 |
| 25 | 1550 |
| 30 | 1350 |

What is claimed is:

1. Derivatives of morpholine containing substituted piperdine groups having the formula

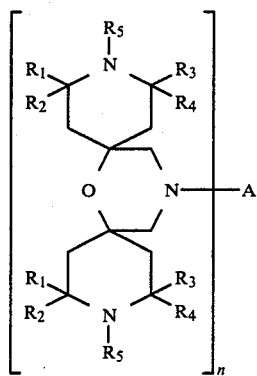

wherein:
$R_1$, $R_2$, $R_3$ and $R_4$, the same or different, are each a lower alkyl group, or $R_1$ and $R_2$ and/or $R_3$ and $R_4$, together with a carbon atom to which they are bound, represent a cycloalkyl group or a group of the formula:

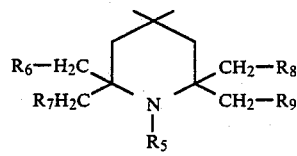

in which $R_6$, $R_7$, $R_8$ and $R_9$, the same or different, represent a hydrogen atom or a lower alkyl group, and $R_5$ represents a hydrogen atom, an alkyl group, an alkenyl group, an alkoxyalkyl group, an aralkyl group, an aralkyl group carrying on the aryl radical up to 3 substituents selected from among chlorine atoms, alkyl groups containing from 1 to 4 carbon atoms, alkoxy groups containing from 1 to 8 carbon atoms, and hydroxy groups, a 2,3-epoxypropyl group, a group of formula —CH$_2$—COOR$_{10}$ in which $R_{10}$ is an alkyl group, an alkenyl group, a phenyl group, and aralkyl group or a cyclohexyl group; a group of formula:

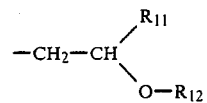

in which $R_{11}$ is a hydrogen atom, a methyl group, an ethyl group or a phenyl group, and $R_{12}$ is a hydrogen atom, an alkyl-substituted piperidyl group, a triazinyl group or an acyl group; and aliphatic acyl group or a group of formula —COOR$_{13}$ in which $R_{13}$ is an alkyl group, a benzyl group or a phenyl group:

A represents an organic group having n valence which does not adversely affect the polymer-stabilization activity selected from among a hydrogen atom, an alkyl residue containing up to 18 carbon atoms optionally containing substituents selected from phenyl and hydroxy groups, an alkenyl residue containing up to 18 carbon atoms, an aliphatic, arylaliphatic, aromatic or alicyclic acy or diacyl residue containing up to 20 carbon atoms, and a heterocyclic residue; and n is an integer ranging from 1 to 3 depending on the valence of A.

2. Derivatives of morpholine according to claim 1, in which each of $R_1$, $R_2$, $R_3$ and $R_4$, is an alkyl group containing from 1 to 4 carbon atoms.

3. Derivatives of morpholine according to claim 1, in which $R_1$ and $R_2$ and/or $R_3$ and $R_4$, together with the carbon atom to which they are bound, represent a cycloalkyl group containing from 5 to 7 carbon atoms, or

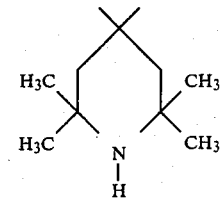

4. Derivatives of morpholine according to claim 1, in which $R_5$ is selected from the following groups:
an alkyl group containing from 1 to 8, carbon atoms;
an alkenyl group containing from 3 to 6 carbon atoms;
an alkoxy-alkyl group containing from 1 to 3 carbon atoms in the alkyl chain and from 1 to 18 carbon atoms in the alkoxyl chain;
an aralkyl group containing from 7 to 15 carbon atoms unsubstituted or an aralkyl group substituted in the alkyl radical by up to 3 substituents with chlorine atoms, alkyl groups containing from 1 to 4 carbon atoms, alkoxy groups containing from 1 to 8 carbon atoms and hydroxy groups;
a group of formula —CH$_2$—COOR$_{10}$ in which $R_{10}$ is an alkyl group containing from 1 to 18 carbon atoms, an alkenyl group containing from 3 to 6 carbon atoms, a phenyl group, an aralkyl group containing from 7 or 8 carbon atoms or a cyclohexyl group;
a group

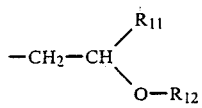

in which $R_{11}$ is hydrogen atom, methyl or phenyl and $R_{12}$ is hydrogen atom, an alkyl group containing from 1 to 4 carbon atoms or an acyl group;

an aliphatic saturated or unsaturated acyl group containing up to 4 carbon atoms;

a group of formula —COOR$_{13}$ in which $R_{13}$ represents an alkyl group having from 1 to 8 carbon atoms, a benzyl group or a phenyl group.

5. Derivatives of morpholine according to claim 1, in which A represents a hydrogen atom; an alkyl or alkenyl residue containing up to 18 carbon atoms, which may be unsubstituted or substituted; an aliphatic, arylaliphatic, aromatic or alicyclic acyl or diacyl residue containing up to 20 carbon atoms, or a heterocyclic group.

6. Derivatives of morpholine according to claim 5, in which A represents:

When n=1
- a hydrogen atom;
- an aliphatic, arylaliphatic, alicyclic, aromatic or heterocyclic acyl group containing up to 18 carbon atoms; a group of formula —COR$_{19}$ in which $R_{19}$ represents a hydrogen atom, an alkyl group with 1 to 17 carbon atoms; an alkenyl group with 2 to 5 carbon atoms; an alkynyl group with 2 to 3 carbon atoms; a phenyl group, a substituted phenyl group with up to 3 substituents, like or unlike, selected from among chlorine, alkyl with 1 to 4 carbon atoms, alkoxy with 1 to 8 carbon atoms, hydroxy or nitro; a naphthyl group; a styryl group, an aralkyl group with 7 to 15 carbon atoms, optionally containing up to 3 like or unlike substituents selected from among chlorine, alkyl with 1 to 4 carbon atoms, alkoxy with 1 to 8 carbon atoms or hydroxy; a phenoxymethyl group, a cyclohexyl group, a 1-pyridyl group; a 3-pyridyl group; a 4-pyridyl group; a 2-furyl group;
- a group of formula —CO—R$_{20}$—COOH, in which $R_{20}$ represents an alkylne group containing from 1 to 10 carbon atoms, the chain of which may be interrupted by an atom of oxygen or of sulphur; or a metal salt thereof, in which the metal is selected from barium, nickel, manganese, calcium, zinc, iron, sodium, cobalt and tin, or a lower alkyl ester thereof in which the alkyl chain contains from 1 to 4 carbon atoms;
- a group of the formula:

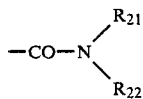

in which $R_{21}$ represents hydrogen; an alkyl group containing 1 to 4 carbon atoms; an aralkyl group containing 7 or 8 carbon atoms, or a phenyl group, and $R_{22}$ represents an alkyl group containing from 1 to 18 carbon atoms, an aryl group containing from 6 to 10 carbon atoms, optionally substituted by one or more chlorine atoms and/or alkyl groups containing from 1 to 4 carbon atoms; an aralkyl group containing 7 or 8 carbon atoms; a cyclohexyl group; or $R_{21}$ and $R_{22}$, together and with the nitrogen atom to which they ar bound, form a piperidinic group, a 1-pyrrolidinylic group or a morpholinic group;

an alkyl group containing from 1 to 18 carbon atoms;

an alkynyl group containing from 3 to 6 carbon atoms;

an aralkyl group with 7 to 9 carbon atoms, optionally carrying up to 3 substituents in the aryl chain selected from among an alkyl having 1 to 4 carbon atoms and/or a hydroxyl group;

a cyclohexyl group;

a group of the formula:

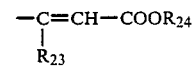

in which $R_{23}$ represents a hydrogen atom, a methyl or lower alkyl group or a phenyl group and $R_{24}$ represents an alkyl group containing from 1 to 8 carbon atoms:

an alkyl substituted alkylene-piperidinyl group of the formula:

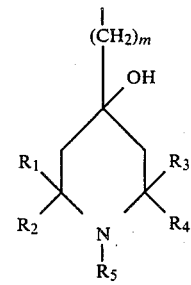

in which m is an integer between 1 and 6 and $R_1$, $R_2$, $R_3$, $R_4$ and $R_5$ have the above-reported meanings; and When n=2
A is selected from: a group of the formula:

in which p is 0 or 1 and $R_{25}$ is a linear or branched alkylene group with 1 to 20 carbon atoms, optionally containing an alkyl-benzyl or hydroxy-alkyl-benzyl group and the chain of which may be interrupted by a sulphur or oxygen atom; an alkenylene group with from 2 to 4 carbon atoms; a phenylene group; a cyclohexylene group; a thiophendiyl group; a 2,4-group; a cyclohexylene group; a thiophendiyl group; a 2,4-pyridindiyl group, or a 2,5-pyridindiyl group;

a carbonyl group;

a group of the formula:

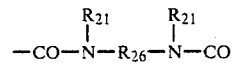

in which $R_{21}$ has the same meaning as defined herein and $R_{26}$ represents an alkylene group containing from 2 to 10 carbon atoms; an arylene group having from 6 to 10 carbon atoms and optionally alkyl substituted; a xylylene group; a cyclohexylene group, a group of the formula:

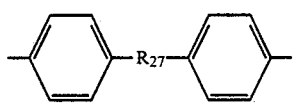

in which $R_{27}$ is an atom of oxygen or an alkylene group containing from 1 to 4 carbon atoms; a group of the formula:

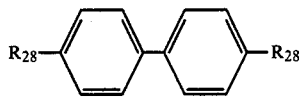

in which $R_{28}$ is a hydrogen atom or a methyl group, or a group of the formula:

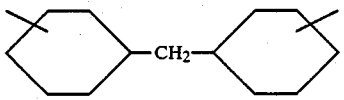

or a group of the formula:

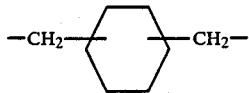

an alkylene group containing up to 10 carbon atoms; an alkenylene group containing from 4 to 10 carbon atoms;
a xylylene group;
a group of the formula:

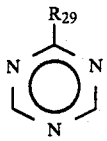

wherein $R_{29}$ is hydrogen, an alkyl group containing up to 18 carbon atoms, the group

the group —O—$R_{32}$, wherein $R_{30}$, $R_{31}$ and $R_{32}$, equal or different, are hydrogen, alkyl containing up to 18 carbon atoms, or the group:

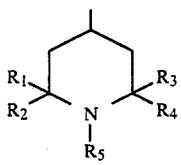

or $R_{30}$ and $R_{31}$ together with N atom to which they are linked from a cyclic group which may contain other hetero atoms such as O or N; and When n=3
A is selected from

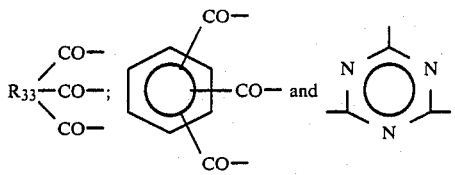

in which $R_{33}$ is a linear or cyclic alkyl group containing up to 18 carbon atoms.

7. Derivatives of morpholine according to claim 1, characterized by having the formula:

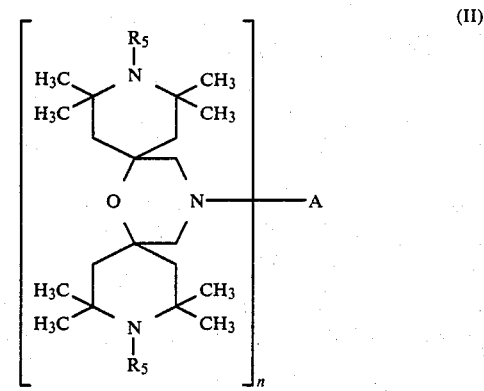

(II)

in which $R_5$ represents a hydrogen atom, a methyl, a benzyl group, a 2,3-epoxypropyl group, or a group of the formula —$CH_2$—$CH_2$—O—$R_{12}$ in which $R_{12}$ is hydrogen or an alkyl group with 2 to 18 carbon atoms or a benzoyl group:

n=1, 2 or 3: and

When n=1
A represents a hydrogen atom; an alkyl radical containing up to 6 carbon atoms; a group of the formula —CO—$R_{19}$ in which $R_{19}$ represents an alkyl group with 1 to 17 carbon atoms, a phenyl group optionally substituted by up to 3 alkyl radicals containing 1 to 4 carbon atoms and/or a hydroxy group, or a 4-hydroxy-3,5-di-tert-butylphenethyl group; or a group of the formula —CO—NH—$R_{22}$ in which $R_{22}$ represents an alkyl group with 1 to 18 carbon atoms, a phenyl group or a cyclohexyl group; and When n=2
A represents an alkylene group containing up to 6 carbon atoms; —CO—, a group of formula —CO—($R_{25}$)$_p$—CO— in which p is 0 or 1 and $R_{25}$ represents an alkenyl group with 1 to 10 carbon atoms; the group —$CH_2$—$CH_2$—S—$CH_2$—$CH_2$— or a phenylene group; a group of the formula —CO—NH—$R_{26}$—NH—CO—, in which $R_{26}$ represents the hexamethylene radical, 2,4-toluylene or methylene-di-p-phenylene; or a triazine radical:

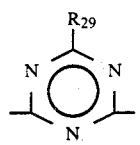

in which $R_{29}$ represents

or $-O-R_{32}$, $R_{31}$ and $R_{32}$ being an alkyl with up to 8 carbon atoms, the group

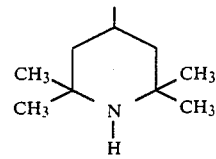

or $R_{30}$ and $R_{31}$ together with the N atom forming the morpholine group; and When $n=3$ A represents:

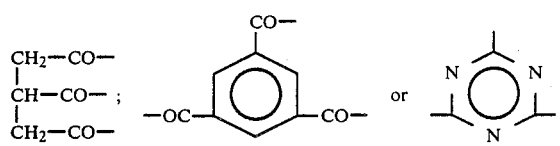

8. Derivatives of morpholine according to claim 7, in which in the formula (II)
   $n=1$ and A represents hydrogen or a group of the formula $-CO-R_{19}$; or
   $n=2$ and A represents a group of the formula $-CO-R_{25}-CO-$, with $R_{19}$ and $R_{25}$ having the same meanings as defined in claim 6.

* * * * *